United States Patent
Babel et al.

(10) Patent No.: US 6,395,520 B1
(45) Date of Patent: May 28, 2002

(54) METHOD FOR THE CONTINUOUS MICROBIOLOGICAL PRODUCTION OF POLYHYDROXY BUTYRIC ACID

(75) Inventors: Wolfgang Babel, Leipzig; Thomas Maskow, Grosskorbetha, both of (DE)

(73) Assignee: UFZ-Umweltforschungszentrum Leipsig-Halle GmbH (DE)

( * ) Notice: Subject to any disclaimer, the term of this patent is extended or adjusted under 35 U.S.C. 154(b) by 0 days.

(21) Appl. No.: 09/787,580

(22) PCT Filed: Apr. 26, 1999

(86) PCT No.: PCT/EP99/02803
§ 371 (c)(1),
(2), (4) Date: Nov. 3, 2000

(87) PCT Pub. No.: WO99/57298
PCT Pub. Date: Nov. 11, 1999

(30) Foreign Application Priority Data

Apr. 30, 1998 (DE) .......................................... 198 20 168

(51) Int. Cl.[7] .................................................. C12P 7/62
(52) U.S. Cl. ........................ 435/135; 435/136; 435/146; 435/170; 435/252.1; 435/822
(58) Field of Search ................................. 435/135, 136, 435/146, 170, 822, 252.1

(56) References Cited

U.S. PATENT DOCUMENTS 5,874,291 A * 2/1999 Bielefeldt et al. .......... 435/262

FOREIGN PATENT DOCUMENTS

EP 0643138 * 3/1995

OTHER PUBLICATIONS

Sang Yup Lee "Bacterial Polyhydroxyalkanoates" Biotech & Bioeng. vol. 49, p. 1–14 (1996).*

* cited by examiner

Primary Examiner—Herbert J. Lilling
(74) Attorney, Agent, or Firm—Norris, McLaughlin & Marcus, P.A.

(57) ABSTRACT

The invention relates to the microbial synthesis of polyhydroxyalkanoic acids [PHA(B)] from substrates which have potential environmental toxicity and must therefore be detoxified and which, if capable of being utilized as a source of carbon and energy by microorganisms for growth and propagation, exhibit the phenomenon of substrate inhibition. According to the invention, a process for the continuous microbiological production of PHB is provided, which process is characterized in that strains of microorganisms known to be PHB producers are propagated chemo-statically at maximum heat production on substrates exhibiting growth inhibition in case of excess substrate, the maximum heat production corresponding to a maximum PHB content in the biomass being adjusted by means of the substrate flow rate.

9 Claims, No Drawings

METHOD FOR THE CONTINUOUS MICROBIOLOGICAL PRODUCTION OF POLYHYDROXY BUTYRIC ACID

This application is a 371 of PCT/EP99/02803 Apr. 26, 1999.

BACKGROUND OF THE INVENTION

The invention relates to the microbial synthesis of polyhydroxyalkanoic acids [PHA(B)] from substrates which have potential environmental toxicity and must therefore be detoxified and which, if capable of being utilized as a source of carbon and energy by microorganisms for growth and propagation, exhibit the phenomenon of substrate inhibition.

More than 150 species of bacteria from more than 50 genera are known to form polyhydroxybutyric acid (PHB) [Steinbüchel, A. (1996) Biotechnology (ed. H.-J. Rehm et al.) Vol. 6, Products of Primary Metabolism (ed. M. Roehr), VCH Weinheim, 403–464]. The formation of PHB is not associated with a particular substrate or a particular type of nutrition [Babel, W. (1992) FEMS Microbiology Rev. 103, 141–148] and may proceed starting from $CO_2$ in a chemolitho-autotrophic fashion and also, from reduced organic carbon compounds. Hydrocarbons such as methane, alcohols such as methanol, and acids such as acetic acid and lactic acid are also possible, as well as sugars. More than 50 different substances have been tested.

Processes for the bacterial synthesis of PHB are well-known [Lee, S. Y. (1996). Biotechnol. Bioeng. 49, 1–14]. Substrates most frequently used are carbohydrates as so-called renewable raw materials. Being readily available and relatively favorable in cost, attempts to render methanol and methane commercially acceptable for the synthesis of polyhydroxyalkanoic acids have been made for quite some time. Nevertheless, the price of the product still is high, so that PHB cannot compete with polypropylene and polyethylene plastic materials which are produced on a huge scale and have similar properties, but no (microbiological degradability, and therefore represent a problem when disposed in the form of waste. Since the price of the product is decisively determined by the price of the raw material [Babel, W. (1997) BIOWORLD 4/97, 16–20], more cost-effective carbon sources for the PHB synthesis have to be developed.

Most of the processes for producing PHB described in the literature accumulate PHB(A) as a result of imbalances in the nutrient supply, and in batch cultivation in the stationary phase. As a result of a developing and continuing deficiency e.g. in nitrogen, oxygen or phosphorus (in the form of phosphate), the propagation rate is reduced, and PHB formation is initiated.

Typically, the formation of PHB proceeds independently of growth, so that rendering a process for the synthesis thereof a continuous one is not easy. EP 0,149,744 A1 describes a continuous process. Certainly, this process is based on a special feature of *Alcaligenes latus* which, in case of complete supply with nutrients optimum for growth and under non-limited conditions of growth, is capable of synthesizing PHB from sugars. This process enables high PHB accumulation either by steady, periodic feeding of substrate (fed-batch regimen), or by a continuous procedure wherein the culture is supplied with a constant flow of fresh nutrient solution and, on the other hand, an aliquot amount of culture medium containing biomass is removed from the fermenter.

Similarly, *Methylobacterium rhodesianum* must have a specific metabolic/regulatory disposition which can be utilized for continuous PHB production [Ackermann, J.-U., Babel, W. (1997) Appl. Microbiol. Biotechnol. 47, 144–149].

As in the case of *A. latus*, sugar (in addition to other substrates) is the raw material for PHB synthesis in *M. rhodesianum* as well.

It has now been found that, as an alternative, PHB can also be produced from substrates having a potential environmental toxicity, and a process regimen has been developed enabling the synthesis of PHB using waste products from the chemical industry and agriculture. Thus, the process according to the invention utilizes cost-effective sources of carbon such as phenol or benzoates, enabling disposal of hazardous substances with simultaneous synthesis of useful materials.

SUMMARY OF THE INVENTION

According to the invention, substrates of potential environmental toxicity are employed which feature the phenomenon of substrate inhibition and thus, in the conventional meaning, are unsuitable for the synthesis of over-flow metabolism products, including PHB as well. They are neither suitable in batch operation nor in single-step chemostatic processes limited to carbon substrates, because such conditions which actually prevent growth and propagation and favor PHB synthesis are not realized. Such substrates are aromatic compounds, including phenols, benzoic acid and benzaldehyde. The latter are well-known for their bactericide (bacteriostatic) effect and frequently represent significant components in industrial waste waters.

According to the invention, a process has been developed which can be used to produce PHB from substrates which, when present in excess, exhibit growth inhibition in that appropriate microorganisms utilizing these substrates are chemostatically propagated in such a way that the heat production relative to the substrate flow rate reaches a maximum. Cell growth is monitored calorimetrically, and the maximum heat production corresponding to a maximum PHB content in the biomass is controlled via the substrate flow rate. PHB formation is initiated and controlled by increasing the substrate flow rate at a small volume change.

In a particularly preferred embodiment of the invention, *Variovorax paradoxus* JMP 116 (DSM No. 4065) is propagated at benzoate flow rates between 0.3 to 1.0 g/lh at rates between 0.07 to 0.4 $h_{-1}$. In another preferred embodiment, *Ralstonia eutropha* JMP 134 (DSM No. 4058) is propagated at phenol flow rates between 0.3 to 0.6 g/lh at rates between 0.05 to 0.2 $h_{-1}$. It is also preferred to propagate *Ralstonia eutropha* JMP 134 at benzoate flow rates between 0.25 to 0.7 g/lh at rates between 0.04 to 0.21 $h_{-1}$. The strains that are used are generally available from culture collections.

DESCRIPTION OF PREFERRED EMBODIMENT

In a particularly preferred embodiment of the invention, *Variovorax paradoxus* JMP 116 is propagated at benzoate flow rates between 0.3 to 1.0 g/lh at rates between 0.07 to 0.4 $h_{-1}$. In another preferred embodiment, *Ralstonia eutropha* JMP 134 is propagated at phenol flow rates between 0.3 to 0.6 g/lh at rates between 0.05 to 0.2 $h_{-1}$. It is also preferred to propagate *Ralstonia eutropha* JMP 134 at benzoate flow rates between 0.25 to 0.7 g/lh at rates between 0.04 to 0.21 $h_{-1}$. The strains that are used are generally available from culture collections.

According to the invention, a constant amount of heat is withdrawn from the fermenter through a helical heat exchanger in order to determine the heat production in a calorimetric mode. To this end, the mass flow of coolant through the heat exchanger and the temperature difference between inlet and outlet are maintained constant, an electrical heater being controlled in such a way that the reactor temperature remains constant. The difference between the current electric heating power and the one prior to inoculation corresponds to the heat production of the microorganisms.

Without intending to be limiting, the invention will be illustrated in more detail with reference to the following embodiments.

EMBODIMENTS

Example 1

The strain *Ralstonia eutropha* JMP 134 is used. Cultivation is effected in a thermally insulated fermenter 2.2 l in capacity at pH 7.0 and 30C. All the media used in the present Example and the other Examples include 1.14 g/l of $NH_4Cl$, 1.7 g/l of $KH_2PO_4$, 2.18 g/l of $K_2HPO_4$, as well as the trace salts (in mg/l) $MgSO_4 7H_2O$ (712), $CaCl_2 2H_2O$ (37), $FeSO_4 7H_2O$ (50), $CuSO_4 5H_2O$ (7.8), $MnSO_4 1H_2O$ (6.1) $ZnSO_4 7H_2O$ (4.4), $NaMoO_4 2H_2O$ (2.5). The fermenter is charged with 1.71 l of nutrient medium including 100 mg/l of phenol. A cooling medium continuously withdraws a constant energy therefrom, and the reactor temperature is maintained using an electrical heater. The fermenter is supplied with gas using 100 Nl/h of humid air, and homogenization is performed by stirring at 900 rpm. The influent medium, i.e., 1N NaOH to maintain the pH value and air, is brought to reactor temperature by means of a heat exchanger. 100 ml of an initial culture wherein the biomass has been brought to about 500 mg/l by fed-batch cultivation is used to inoculate the fermenter. The heating energy required to maintain a constant reactor temperature is decreased by the heat produced by the microorganisms as soon as they commence utilizing the phenol. Once the heat production drops to 0 W/l again, thereby indicating that the phenol has been consumed, growth is reinitiated using a 200 ml portion of medium including 1 g/l of phenol. By repeating this procedure, the biomass is increased to about 0.7 g/l, a reactor filling level of 21 l is adjusted, and subsequently, 200 ml/h of medium including 1 g/l of phenol is added continuously. The culture medium flows off in an equal amount, thereby implementing a substrate consumption rate of 0.1 g/(lh). After 30 hours, the constant heat production indicates that a steady state has been reached. The culture medium at this point has a residual phenol concentration of <0.1 mg/l and a biomass concentration of 0.7 g/l with no detectable amounts of PHB. Thereafter, 200 ml/h is fed into the fermenter from a thoroughly stirred mixing vessel (200 rpm) containing a medium including 1 g/l of phenol. A medium including 10 g/l of phenol flows into the mixing vessel at 100 ml/h. Heat production increases in a linear fashion until a bend indicates the beginning PHB production. Thereafter, the PHB content increases until heat production reaches a maximum of 2.7 W/l, the above taking place at a substrate flow rate of about 0.69 g/(lh). For stabilization purposes, the inflow into the fermenter is stopped and subsequently, the substrate flow rate is reduced to that value where 96% of the heat production have been reached. Under these conditions, the culture medium contains <0.1 mg/l of residual phenol and a biomass concentration of 2.9 g/l, with a PHB content of 17% of bacteria dry mass.

Example 2

The strain *Ralstonia eutropha* JMP 134 is cultivated chemostatically in an analogous fashion as in Example 1. However, the media include 0.88 g/l of sodium benzoate in the mixing vessel and 12 g/l of sodium benzoate in the reservoir bottle, and the inflow into the fermenter is 100 ml/h. The pH value is maintained constant by titrating 0.5 N hydrochloric acid. Measurement of the heat production, preheating of the media, the acid and humid air are performed as described in Example 1. The maximum heat production, being about 0.94 W/l, is reached at a substrate flow rate of about 0.353 g/(lh). The culture medium in this case contains a residual sodium benzoate concentration of 25 mg/l and 4.2 g/l of biomass having a PHB content of 25%.

Example 3

The strain *Variovorax paradoxus* DSM 4065 is propagated continuously as specified in Example 1. However, the media include 1.2 g/l of sodium benzoate in the mixing vessel and 9.5 g/l of sodium benzoate in the reservoir bottle with an otherwise equal composition of the medium as in Example 1. Likewise, the determination of the heat flow, heating of the media, humid air and titrating agent corresponds to Example 1. The inflow into the fermenter is 240 ml/h, and the pH value is maintained constant by adding 0.5 N HCl. The maximum heat production of about 3.9 W/l is reached at a substrate flow rate of 1.14 g/(lh) where the culture medium contains a residual sodium benzoate concentration of 45 mg/l and 3.6 g/l of biomass having a PHB content of 21%.

What is claimed is:

1. A process for the continuous microbiological production of polyhydroxybutyric acid (PHB), wherein in that strains of microorganisms known to be PHB producers are propagated continuously at constant reaction volume and maximum heat production on substrates exhibiting growth inhibition in case of excess substrate, with the exception of methanol, the maximum heat production corresponding to a maximum PHB content in the biomass being adjusted by means of the substrate flow rate.

2. The process according to claim 1, wherein the substrates are aromatic compounds.

3. The process according to claim 1, wherein the strain of microorganisms are chosen from the group consisting of the genera Comamonas, Ralstonia and Variovorax.

4. The process according to claim 1, wherein the continuous production is performed in a temperature range between 25 and 40° C. and at pH values between 6 and 8 with ventilation and homogenization.

5. The process according to claim 1, wherein *Variovorax paradoxus* JMP 116 is propagated at benzoate flow rates between 0.3 to 1.0 g/lh at rates between 0.07 to 0.4 $h^{-1}$.

6. The process according to claim 1, wherein *Ralstonia eutropha* JMP 134 is propagated at phenol flow rates between 0.3 to 0.6 g/lh at rates between 0.05 to 0.2 $h^{-1}$.

7. The process according to claim 1, wherein, *Ralstonia eutropha* JMP 134 is propagated at benzoate flow rates between 0.25 to 0.7 g/lh at rates between 0.04 to 0.21 $h^{-1}$.

8. The process according to claim 2, wherein the aromatic compounds are selected from the group consisting of phenols, benzoic acid and benzaldehyde.

9. The process according to claim 2, wherein the strains of microorganisms are selected from the group consisting of *Comamonas acidovorans, Comomonas testosteroni, Ralstonia eutropha,* and *Variovorax paradoxus*.

* * * * *